United States Patent
Komatsu et al.

(10) Patent No.: US 7,517,674 B2
(45) Date of Patent: *Apr. 14, 2009

(54) PROCESS OF HYDROLYZING OIL OR FAT USING A PACKED LAYER OF IMMOBILIZED ENZYME

(75) Inventors: Toshiteru Komatsu, Kashima-gun (JP); Hiroaki Yamaguchi, Kashima-gun (JP); Naoto Yamada, Kashima-gun (JP)

(73) Assignee: Kao Corporation, Tokyo (JP)

( * ) Notice: Subject to any disclaimer, the term of this patent is extended or adjusted under 35 U.S.C. 154(b) by 278 days.

This patent is subject to a terminal disclaimer.

(21) Appl. No.: 11/144,780

(22) Filed: Jun. 6, 2005

(65) Prior Publication Data

US 2005/0277180 A1    Dec. 15, 2005

Related U.S. Application Data

(63) Continuation-in-part of application No. 10/166,687, filed on Jun. 12, 2002, now Pat. No. 6,921,652.

(30) Foreign Application Priority Data

Jun. 22, 2001  (JP) ............................. 2001-190335

(51) Int. Cl.
| | |
|---|---|
| C12P 7/64 | (2006.01) |
| C12P 7/62 | (2006.01) |
| C12N 11/14 | (2006.01) |
| C12N 11/02 | (2006.01) |
| C12N 11/08 | (2006.01) |

(52) U.S. Cl. .................. 435/134; 435/135; 435/176; 435/177; 435/180

(58) Field of Classification Search ............... None
See application file for complete search history.

(56) References Cited

U.S. PATENT DOCUMENTS 6,258,575 B1    7/2001  Shimizu et al.

OTHER PUBLICATIONS

U.S. Appl. No. 11/743,997, filed May 3, 2007, Nishide, et al.

*Primary Examiner*—David M Naff
(74) *Attorney, Agent, or Firm*—Oblon, Spivak, McClelland, Maier & Neustadt, P.C.

(57) ABSTRACT

A process is disclosed for hydrolyzing an oil or fat by mixing and feeding an oil-phase substrate and a water-phase substrate to a packed layer with an immobilized enzyme packed therein. The oil or fat is subjected to a hydrolytic reaction under feeding conditions such that a shear stress factor ($\tau w$), which is applied to a surface of said immobilized enzyme and is expressed by the following formula (1):

$$\tau w = (\Delta P/L) \times dp \times \epsilon/(1-\epsilon) \quad (1)$$

wherein $\Delta P$ represents a maximum pressure loss [MPa] through said packed layer during said hydrolytic reaction, L represents a thickness [m] of said packed layer, dp represents a weight-basis average particle size [m] of particles of said packed, immobilized enzyme, and $\epsilon$ represents a void volume [-] of said packed layer, remains within a range of from $1 \times 10^{-4}$ to $1.4 \times 10^{-3}$ MPa. The reaction of the oil-phase substrate and the water-phase substrate in the packed layer of the immobilized enzyme of high activity under the predetermined conditions allows the immobilized enzyme to more effectively exhibit its activity, so that the efficiency of the hydrolytic reaction is heightened to increase the productivity and the serviceability of the immobilized enzyme is also improved.

10 Claims, 3 Drawing Sheets

PROCESS OF HYDROLYZING OIL OR FAT USING A PACKED LAYER OF IMMOBILIZED ENZYME

REFERENCE TO RELATED APPLICATIONS

This application is a continuation-in-part of a U.S. patent application Ser. No. 10/166,687 filed on Jun. 12, 2002, now U.S. Pat. No. 6,921,652, which is incorporated herein by reference and which claims priority under 35 USC 119(a) to Japanese patent application No. 2001-190335 filed on Jun. 22, 2001 in Japan, the teachings of which are hereby incorporated by reference herein and priority to which is claimed herein.

BACKGROUND OF THE INVENTION a) Field of the Invention

This invention relates to a process for subjecting oil or fat to a hydrolytic reaction in a layer packed with an immobilized enzyme, which features allowing the immobilized enzyme to more effectively exhibit its activity so that the productivity is increased while making an improvement in the serviceability of the immobilized enzyme.

b) Description of the Related Art

Hydrolytic processes of oil and fat, which make use of immobilized enzymes, include continuous processes, which use reactors such as packed-column (fixed-bed) reactors, fluidized-bed reactors and falling-film reactors, in addition to non-continuous processes using agitated reactors. With conventional techniques, however, such immobilized enzymes are low in hydrolytic activity and moreover, their hydrolytic activity is lowered further due to separation or the like of the enzymes.

JP-A-61085195A discloses a process which comprises countercurrently feeding water and oil or fat as liquid reactants from the top and bottom of a vertical packed column, respectively, to bring them into contact with each other. The liquid reactants are brought as continuous phases into contact with an immobilized enzyme. To avoid emulsification of water and the oil or fat, their feeding rates are $7.6 \times 10^{-3}$ mm/min, i.e., are extremely low, and the residence time required for the reaction ranges from several tens to several hundreds of hours, that is, is long. This process also involves additional problems that special facilities and operation method are required to countercurrently feed the two liquids to the packed column.

On the other hand, a system in which water and oil or fat are concurrently fed in the same direction to bring them into contact with each other is also accompanied by a problem that the residence time is long.

Processes, each of which makes use of a fluidized bed reactor [for example, J. Am. Oil Chem. Soc., 72, 1281 (1995)], require residence time as long as 40 hours, and have not succeeded yet in achieving any high hydrolysis yield in short time.

Processes, each of which makes use of a membrane reactor [for example, J. Am. Oil Chem. Soc., 62, 1016 (1985)], are low in the permeability of a liquid reaction mixture through enzyme-immobilized membranes, resulting in very low hydrolytic reaction rates.

Further, no publication is known to disclose a method for controlling a reduction in the activity of an immobilized enzyme, specifically a method for improving its serviceability.

In the conventional processes each of which hydrolyzes oil or fat by feeding it to an immobilized enzyme and bringing it into contact with the immobilized enzyme, any attempt to increase the efficiency of the reaction by the enzyme requires prolonging the time of contact between the enzyme and the oil or fat to increase the residence time of the liquid reactant(s) as described above. In addition, the activity of each immobilized enzyme is lowered in short time so that its serviceability is poor. Frequent replacement of the immobilized enzyme is, therefore, needed to retain high productivity.

SUMMARY OF THE INVENTION

An object of the present invention is, therefore, to provide a high-productivity hydrolytic process of oil or fat by efficiently conducting contact between an immobilized enzyme and the oil or fat and heightening the serviceablity of the immobilized enzyme.

The present inventors have found that upon feeding oil or fat to an immobilized enzyme, control of the feeding such that a shear stress factor applied to surfaces of particles of the immobilized enzyme remains within a range of specific values of a formula—which is derived from an equivalent circular tube diameter of passages formed of voids in a packed layer through which the liquid flows and shear stress applied to an inner wall of a circular tube having the equivalent circular tube diameter when a fluid is flowing through the circular tube—allows the immobilized enzyme to effectively exhibit its activity and also to be improved in its serviceability and hence, can provide a high-productivity hydrolytic process for the oil or fat.

The present invention, therefore, provides a process for hydrolyzing an oil or fat by mixing and feeding an oil-phase substrate and a water-phase substrate to a packed layer with an immobilized enzyme packed therein, wherein the oil or fat is subjected to a hydrolytic reaction under feeding conditions such that a shear stress factor ($\tau w$), which is applied to a surface of the immobilized enzyme and is expressed by the following formula (1):

$$\tau w = (\Delta P/L) \times dp \times \epsilon/(1-\epsilon) \qquad (1)$$

wherein $\Delta P$ represents a maximum pressure loss [MPa] through the packed layer during the hydrolytic reaction, L represents a thickness [m] of the packed layer, dp represents a weight-basis average particle size [m] of particles of the packed, immobilized enzyme, and $\epsilon$ represents a void volume [-] of the packed layer, remains within a range of from $1 \times 10^{-4}$ to $1.4 \times 10^{-3}$ MPa.

The reaction of the oil-phase substrate and the water-phase substrate in the packed layer of the immobilized enzyme of high activity under the predetermined conditions allows the immobilized enzyme to more effectively exhibit its activity, so that the efficiency of the hydrolytic reaction is heightened to increase the productivity and the serviceability of the immobilized enzyme is also improved.

DESCRIPTION OF THE SYMBOLS

1. Agitator
2. Substrate circulating tank

3. Substrate-input opening
4. Nitrogen outlet line
5. Substrate (reaction mixture) feed line
6. Substrate feed pump
7. Flowmeter
8. Pressure gauge
9. Column packed with an immobilized enzyme
10. Substrate (reaction mixture) return line
11. Nitrogen feed line
12. Liquid reaction mixture draw line
13. Internal enzyme-packed column residue draw line
14. Reaction mixture sampling line
15. Substrate circulation bypass line
16. Emulsifier
17. Circulating pump
18. Column packed with an immobilized enzyme (5 columns of packed thickness of 200 mm each)
19. Substrate-supplying tank
20. Substrate feed line
21. Feed-metering pump
22. Pressure gauge (at packed thickness of 0 mm, inlet)
23. Pressure gauge (at packed thickness of 200 mm)
24. Pressure gauge (at packed thickness of 400 mm)
25. Pressure gauge (at packed thickness of 600 mm)
26. Pressure gauge (at packed thickness of 800 mm)
27. Reaction mixture collection tank
28. Nitrogen feed line
29. Nitrogen exhausting line
30. Substrate-feeding opening
31. Agitator

DESCRIPTION OF PREFERRED EMBODIMENTS

Oils and fats to which the hydrolytic process according to the present invention is applicable can include oils and fats (triglycerides), diglycerides and monoglycerides and mixtures thereof, each of which may contain one or more free fatty acids. Of these, triglycerides are preferred.

The oil-phase substrate may contain one or more fatty acid monoalkyl esters or the like in addition to the oil or fat.

The water-phase substrate is water, a water-soluble substance such as glycerin, or a mixture thereof, with water being preferred. Water can be any one of tap water, well water, distilled water, deionized water and the like, with deionized water being preferred.

The liquid reaction mixture in the present invention is obtained by mixing the oil-phase substrate, which contains the oil or fat, and the water-phase substrate at a predetermined mixing ratio. The mixing ratio of the water-phase substrate to the oil-phase substrate can be empirically chosen to achieve a desired degree of hydrolysis. In general, however, it is preferred to mix 25 to 100 parts by weight of the water-phase substrate with 100 parts by weight of the oil or fat in the oil-phase substrate.

Any enzyme can be used as an enzyme to be immobilized without any particular limitation insofar as it can hydrolyze the oil or fat. Examples include lipase and esterase. The selectivity of the enzyme can be chosen as desired, including the random type and the α-position selection type. When a high degree of hydrolysis is desired, a random-type enzyme is preferred. Preferred as the enzyme is lipase. Examples include lipases derived from microorganisms such as those belonging to the genus of *Rhizopus*, the genus of *Aspergillus*, the genus of *Chromobacterium*, the genus of *Mucor*, the genus of *Pseudomonas*, the genus of *Geotrichum*, the genus of *Penicilium*, and the genus of *Candida*; and animal lipases such as pancreatic lipase. Particularly preferred are lipases derived from bacteria belonging to the genus of *Pseudomonas* and the fungi belonging to the genus of *Candida*.

The immobilization of the enzyme can be conducted by immobilizing the enzyme on a suitable carrier. Usable examples of the carrier include ion exchange resins, ceramics and so on. To permit exhibition of high enzymatic activity, however, an ion exchange resin is preferred. The material, properties and ion-exchanging groups of the ion exchange resin can be chosen in view of the adsorbability and exhibiting rate of activity of the enzyme to be adsorbed. However, preferred is an anion exchange resin. Examples include phenol-formaldehyde-based anion exchange resins, polystyrene-based anion exchange resins, acrylamide-based anion exchange resins, and divinylbenzene-based anion exchange resins. Particularly preferred are phenol-formaldehyde-based anion exchange resins (for example, "Duolite A-568", trade name; product of Diamond Shamrock Corporation). To lower the shear stress factor applied to the surface of the immobilized enzyme in the packed layer as in the present invention, the weight-basis average particle size of the carrier (as measured by a sieve analysis) may preferably be in a range of from 100 to 1,000 μm, especially in a range of from 150 to 500 μm. On the other hand, the pore size of carrier (as measured by the BET analysis) may preferably be in a range of from 50 to 1,500 Å, especially in a range of from 100 to 1,000 Å from the standpoint of the immobilizable amount of the enzyme.

To assure exhibition of high activity, the immobilized enzyme may be subjected to known treatment (JP-A-09-000257, JP-A-01-153090, etc.). As an alternative example, Japanese Patent Application No. 10-350920 discloses a process, which comprises adsorbing and immobilizing an enzyme on an immobilization carrier composed of a porous anion-exchange resin, followed by treatment with oil or fat. As a still further alternative example, immobilization may be conducted after treating a carrier beforehand with oil or fat, a monohydric alcohol ester of a fatty acid having 8 to 18 carbon atoms, the polyglycerin ester of a fatty acid having 8 to 18 carbon atoms, the sorbitol ester of a fatty acid having 8 to 18 carbon atoms, or the sucrose ester of a fatty acid having 8 to 18 carbon atoms. For this pretreatment, the substance may be used in a proportion of from 0.01 to 1 part by weight, especially from 0.05 to 0.5 part by weight per part by dry weight of the carrier.

The immobilization temperature is determined depending on the properties of the enzyme. It is desired to conduct the immobilization at a temperature where the enzymatic activity is not lost, i.e., at 0 to 60° C., preferably at 5 to 40° C.

The pH of the liquid reaction mixture is determined depending on the properties of the enzyme. It is, however, preferred to control it within a range of from pH 3 to pH 9. It is preferred to maintain this pH by using a pH buffer such as acetate buffer, phosphate buffer or Tris-HCl buffer.

Concerning the ratio of the enzyme to the immobilization carrier, it is preferred to use 0.05 to 10 parts by weight, especially 0.1 to 5 parts by weight of the enzyme per part by weight of the immobilization carrier.

When the carrier is treated with oil or fat subsequent to the immobilization, usable examples of the oil or fat include rapeseed oil, soybean oil, corn oil, olive oil, beef tallow, and fish oil. When oil or fat is hydrolyzed, however, it is preferred to use the same oil or fat as the oil or fat to be hydrolyzed.

The hydrolytic activity of the immobilized enzyme may be preferably 20 U/g or higher, more preferably 100 to 10,000 U/g, especially 500 to 5,000 U/g, still more preferably 1,000 to 5,000 U/g. Here, 1 U of the enzyme indicates the hydrolyzing ability of the enzyme to form 1 μmol of free fatty acids in a minute when a 100:25 parts by weight liquid mixture of the oil or fat and water is hydrolyzed at 40° C. for 30 minutes while agitating and mixing the liquid mixture.

The hydrolytic activity [U/g-oil] of the immobilized enzyme, said hydrolytic activity having been imparted per unit gram of the oil or fat, and the time required until a degree of hydrolysis is reached is in a substantially inverse relationship. When hydrolysis is conducted using a packed layer with an immobilized enzyme, the hydrolysis rate differs depending on the feeding conditions. Nonetheless, the apparent activity (activity to be exhibited) [U/g] of the immobilized enzyme can be determined from the time required for the hydrolysis, the weight [g-oil] of the oil or fat used and the packed weight [g] of the immobilized enzyme. The time required for the hydrolysis can be defined as time required for a reaction mixture to circulate the system, in a case where a circulating reaction is employed, which contains a packed layer with an immobilized enzyme and a circulation tank for circulating a reaction mixture; or a period of time in which a reaction mixture is retained in the packed layer with an immobilized enzyme, in a case where a continuous reaction is employed, in which oil-phase substrate and water-phase substrate are continuously supplied to a packed layer with an immobilized enzyme, without circulating the system. When a hydrolysis operation is continuously repeated, the activity [U/g] to be exhibited by the immobilized enzyme drops with the time t [h] of cumulative use (feeding). Except for an initial time in which considerable separation or the like of the enzyme takes place, the activity [U/g] to be exhibited by the immobilized enzyme is expressed by $E=E_0 \exp(-kt)$ in which $E_0$ [U/g] is the initially exhibited activity of the immobilized enzyme and k [1/h] is the deactivation rate constant.

As the initially exhibited activity $E_0$ becomes higher, the packed layer can be made more compact. As the deactivation rate constant k becomes smaller, the activity undergoes smaller fluctuations so that the productivity is improved.

Upon subjecting a liquid reaction mixture to hydrolysis by feeding the liquid reaction mixture to a packed layer of an immobilized enzyme, a flow of the liquid reaction mixture can be theorized as a flow through a circular tube flow by considering complex passages of voids in the packed layer as a group of parallel small-diameter tubes [SHIRAI, Takashi (1982). "Ryudoso (Fluidized Layers)", p. 53, Kagaku Gijutsusha; KAMEI, Saburo (1975). "Kagaku Kikai no Riron to Keisan (Theories and Calculations on Chemical Equipment) ($2^{nd}$ ed.)", p. 513, Sangyo Tosho Company]. A hydraulic radius $R_h$ [m] obtained by dividing a cross-sectional area, through which a fluid passes, with the length of a tube wall with which the fluid is brought into contact (wetted perimeter) is expressed by the following formula (2):

$$R_h = \epsilon/(S_v \times (1-\epsilon)) = D_{eq}/4 \quad (2)$$

wherein $S_v$ [m²/m³] is the volume-basis specific surface area of packed particles, $\epsilon$ [–] is the void volume of a packed layer and $D_{eq}$ is the equivalent circular tube diameter [m]. Here, the equivalent circular tube diameter $D_{eq}$ [m] is equivalent to 4 times of $R_h$. On the other hand, the void volume $\epsilon$ [–] is calculated in accordance with $\epsilon=(\rho_0-\rho_1)/\rho_0$ wherein $\rho_0$ [kg/m³] and $\rho_1$ [kg/m³] are the true specific gravity and packed bulk specific gravity of the particles, respectively.

The volume-basis specific surface area $S_v$ of the packed particles is expressed by the following formula (3):

$$S_v = \phi/dp \quad (3)$$

wherein dp [m] is the weight-basis average particle size as a representative diameter of the particles and $\phi$ [–] is a shape factor of the particles [KAMEI, Saburo (1975). "Kagaku Kikai no Riron to Keisan (Theories and Calculations on Chemical Equipment)($2^{nd}$ ed.)", p. 395, Sangyo Tosho Company].

The weight-basis average particle size dp is calculated in accordance with the following formula (4):

$$dp = 1/\Sigma(wi/dpi) \quad (4)$$

wherein dpi [m] is a particle size calculated as an average of an undersize sieve opening and an oversize sieve opening by separating the particles are into particle groups, and wi [–] is a mass fraction of the particle size dpi ["Kagaku Kogaku Binran (Handbook of Chemical Engineering) ($5^{th}$ ed.)", p. 242, MARUZEN CO., LTD. (1988)].

$\phi$ is a factor which varies depending on the shape of particles, and is 6 in the case of a sphere. Shape factors of several types of stones—the particle sizes of which are, for example, in a range of from 10 μm to 1,000 μm—are measured to range from 6 to 24 [KAMEI, Saburo (1975). "Kagaku Kikai no Riron to Keisan (Theories and Calculations on Chemical Equipment)($2^{nd}$ ed.)", p. 396, Sangyo Tosho Company].

Shear stress τ [MPa], which is applied to the inner wall of a circular tube when an incompressible fluid is flowing as a laminar flow through the circular tube, is expressed by the following formula (5):

$$\tau = (\Delta P'/L') \times (D/4) \quad (5)$$

wherein ΔP' [MPa] is a pressure loss of the flow through the circular tube, L' [m] is the length of the circular tube and D [m] is the diameter of the circular tube ["TRANSPORT PHENOMENA", pp. 42-47, JOHN WILEY & SONS, INC. (1960)].

Now assuming that the equivalent circular tube diameter $D_{eq}$ obtained by assuming the passages of voids in the packed layer as the circular tube is the diameter D of the circular tube, the length L' of the circular tube is the thickness L of the packed layer and the pressure loss ΔP' of the flow through the circular tube is the maximum pressure loss through the packed layer, introduction of the formulas (2) and (3) into the formula (5) gives the following formula (6):

$$\tau = (1/\phi) \times (\Delta P/L) \times dp \times \epsilon/(1-\epsilon) \quad (6)$$

The formula (6) represents shear stress applied to the inner wall of the circular tube when the passages of voids in the packed layer are assumed to be the circular tube, and means shear stress applied to the surfaces of the packed particles.

According to the present invention, the liquid reaction mixture is fed under conditions such that the shear stress factor expressed by the formula (1) remains within a range of from $1 \times 10^{-4}$ to $1.4 \times 10^{-3}$ MPa, preferably within a range of from $1 \times 10^{-4}$ to $1 \times 10^{-3}$ MPa, most preferably within a range of from $2 \times 10^{-4}$ to $1 \times 10^{-3}$ MPa.

The shear stress factor expressed by the formula (1) is adjusted by changing the pressure loss occurred per the packed thickness through the packed layer when the liquid reaction mixture is fed to the packed layer, the weight-basis average particle size of the immobilized enzyme and the void volume of the packed layer. On the other hand, the pressure loss occurred per the packed thickness through the packed layer is adjusted by changing the average droplet size of the water phase as a dispersed phase in the liquid reaction mixture as a water-in-oil emulsion, the linear feeding rate of the liquid reaction mixture to the packed layer, the particle size of the immobilized enzyme, the void volume, and/or the like.

The void volume of the packed layer is adjusted, for example, by manually packing the immobilized enzyme little by little or by converting the liquid reaction mixture into a slurry with an appropriate fluid (for example, the oil or fat) and feeding the slurry under pressure.

The liquid reaction mixture in the hydrolytic process of according to the present invention is a water-in-oil emulsion and, as the average droplet diameter of the water phase as a dispersed phase becomes smaller, the viscosity of the liquid reaction mixture increases. In a case of a circulating reaction which contains a packed layer with an immobilized enzyme and a circulation tank for circulating a reaction mixture, the viscosity of the liquid reaction mixture is adjusted by changing the charge amount of the liquid reaction mixture obtained by mixing the oil-phase substrate and the water-phase substrate, the agitation speed in a circulating tank, the average linear flow rate when the liquid reaction mixture flows through a circulating line, the shear stress in a circulating pump, and/or the like. In a case of a continuous reaction in which oil-phase substrate and water-phase substrate are continuously supplied to a packed layer with an immobilized enzyme without circulating the system, the viscosity of a liquid reaction mixture is adjusted by changing the mixing proportion of the oil-phase substrate and the water-phase substrate (amount charged), the agitation speed in a substrate-supplying tank, the average linear flow rate when the liquid reaction mixture flows through a feed line, the shear stress in a feed-metering pump, and/or the like. To reduce the pressure loss per the packed thickness, it is preferred to lower the viscosity of the liquid reaction mixture. The average droplet diameter of the water phase as the dispersed phase may range preferably from 40 to 200 μm, more preferably from 45 to 200 μm, most preferably from 60 to 200 μm. The term "average droplet size" as used herein means a value measured by laser diffractometry (for example, by "SALD-1100", trade name; manufactured by Shimadzu Corporation).

The linear feeding rate of the liquid reaction mixture through the packed layer may range preferably from 5 to 400 mm/min, specifically from 10 to 300 mm/min. The term "linear feeding rate" as used herein means a value expressed in terms of the quotient obtained by dividing the amount of the liquid reaction mixture fed per minute (mm³/min) with the cross-sectional area of the packed layer. To more effectively draw the activity of the packed enzyme from the viewpoint of the equilibrium of the hydrolytic reaction, the residence time of the liquid reaction mixture in the packed layer may range preferably from 0.1 to 8 minutes, specifically from 0.4 to 3 minutes, in a case of a circulating reaction. The term "residence time" as used herein means the quotient obtained by dividing the thickness (mm) of the packed layer with the linear feeding rate (mm/min) Further, the product of the residence time of the liquid reaction mixture in the packed layer and the activity of the immobilized enzyme may be preferably 10,000 min×U/g or smaller, specifically in a range of from 500 to 9,000 min×U/g.

In a case of a continuous reaction, a period of time in which a reaction mixture is retained in a packed layer can be adjusted insofar as a desired decomposition rate is achieved; however, it is preferably from 5 to 200 minutes, more preferably from 15 to 100 minutes in order to achieve high decomposition rate.

EXAMPLE 1

Preparation of Immobilized Enzyme

One part by weight of "Duolite A-568" (trade name, product of Diamond Shamrock Corporation; particle size distribution: 100 to 1,000 μm) was agitated for 1 hour in 10 parts by weight of 1/10 N NaOH solution. Subsequent to filtration, the carrier was washed with 10 parts by weight of deionized water. After filtration, the carrier was equilibrated in pH with 10 parts by weight of 500 mM sulfate buffer (pH 7). After filtration, the carrier was equilibrated in pH with 10 parts by weight of 50 mM acetate buffer (pH 7) twice, each for 2 hours, with filtration conducted between the equilibrating operations. Filtration was then conducted to collect the carrier, and the carrier was subjected to ethanol replacement with 5 parts by weight of ethanol for 30 minutes. Subsequent to filtration, 5 parts by weight of ethanol with 1 part by weight of ricinolic acid contained therein were added, and the carrier was allowed to adsorb the ricinolic acid thereon. Filtration was conducted to collect the carrier, and the filtrate was then washed with 5 parts by weight of 50 mM acetate buffer (pH 7) four times, each for 30 minutes, with filtration conducted between the respective washing operations to remove the ethanol. Filtration was then conducted to collect the carrier. Subsequently, the carrier was kept in contact with an enzyme solution, which contained 1 part by weight of commercial lipase ("Lipase AY Amano", trade name; product of Amano Enzyme Inc.) dissolved in 9 parts by weight of 50 mM acetate buffer (pH 7), for 5 hours to conduct immobilization. The immobilized enzyme was collected by filtration, washed with 10 parts by weight of 50 mM acetate buffer (pH 7) to remove unimmobilized enzyme and proteins, and collected by filtration. Thereafter, 4 parts by weight of refined soybean oil to be subjected actually to hydrolysis were added, and the thus-obtained mixture was agitated for 12 hours. The above operations were all conducted at 20° C. Filtration was then conducted to separate the immobilized enzyme from the oil. The thus-obtained immobilized enzyme had 2,042 U/g (dry weight) of hydrolytic activity (exhibitable activity). The weight-basis average particle size of the immobilized enzyme was 451 μm. Incidentally, the immobilized enzyme had a particle size distribution as shown in Table 1.

TABLE 1

| Undersize [μm] | Oversize [μm] | Weight fraction, % |
|---|---|---|
| 500 | 1000 | 44.61 |
| 425 | 500 | 20.44 |
| 355 | 425 | 11.08 |
| 250 | 355 | 18.13 |
| 150 | 250 | 5.44 |
| 106 | 150 | 0.30 |
| 0 | 106 | 0 |

Figure 1:
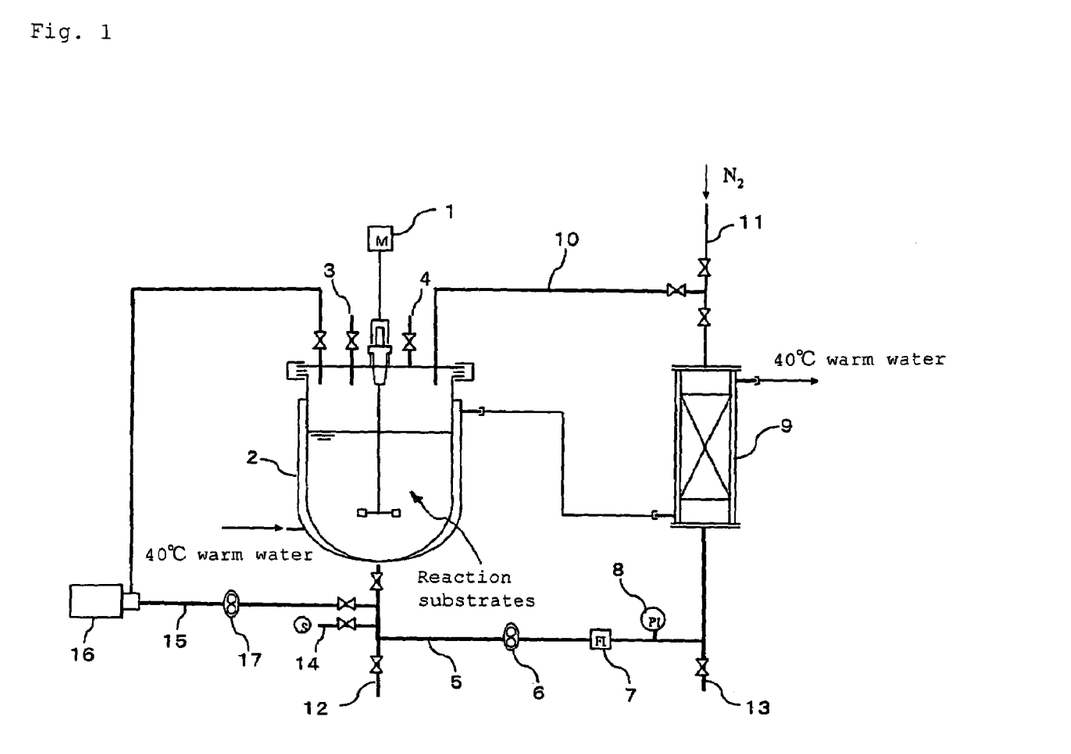
FIG. 1 is a flow diagram of a circulating hydrolysis reactor.

Equipment used for the circulating hydrolytic reaction is illustrated in FIG. 1.

An enzyme column of 22 mm in inner diameter and 145 mm in height was packed with 19.7 g (dry weight basis) of the immobilized enzyme. In accordance with $\epsilon=(\rho_0-\rho_1)/\rho_0$ in which the true specific gravity $\rho_0$ of the immobilized enzyme was 0.619 g/cm³ and the packed bulk specific gravity $\rho_1$ of the immobilized enzyme was 0.357 g/cm³, the void volume $\epsilon$ of the packed layer was calculated to be 0.423 ($\epsilon$=0.423).

The refined soybean oil and deionized water (total weight: 960 to 2,560 g) were charged into a substrate circulating tank 2, which was 150 mm in inner diameter and 3 L in capacity and was equipped with an agitating blade of 50 mm in diameter, such that the weight ratio of the substrates (refined soybean oil [g]/deionized water [g]) became 0.6. The substrates were then heated to 40° C. in 10 minutes while mixing them at 400 r/min. During that heating and mixing, valves were operated to purge a gas-phase portion inside the circulating tank with nitrogen by feeding nitrogen from a nitrogen feed line 11 into the circulating tank 2 via a substrate return line 10 while blowing off the interior gas through a nitrogen outlet line 4. After the substrates were heated to 40° C., the valves were operated to stop the feeding of nitrogen and to close the nitrogen outlet line 4. Subsequently, a valve arranged in a lower part of the substrate circulating tank was opened, and through a substrate feed line 5, the substrates were supplied by a feed pump 6 at a flow rate of 55 mL/min (flowmeter 7) to the column 9 packed with the immobilized enzyme, and through the substrate return line 10, the substrates were fed back to the substrate circulating tank 2 to initiate the hydrolytic reaction under circulation. During the reaction, the flow rate and pressure were monitored by the flowmeter 7 and a pressure gauge 8, respectively, and the liquid reaction mixture was periodically sampled through a sampling line 14 to determine the degree of hydrolysis of the oil. The degree of hydrolysis of the oil was calculated in accordance with (acid value/saponification value)×100 (%). The reaction under circulation was continued until the degree of hydrolysis reached 90% or higher. The maximum pressure loss occurred through the enzyme-packed layer was 0.27 MPa.

On the other hand, the average droplet size of the water-in-oil emulsion (the average size of water droplets in the w/o emulsion) was 120 μm.

The shear stress factor expressed by the formula (1) was $6.15 \times 10^{-4}$ MPa.

Subsequent to the completion of the hydrolysis, the feed pump was stopped, and the liquid reaction mixture in the circulating tank was drawn through a line 12. Further, valves were operated to introduce nitrogen into the enzyme-packed column through the line 11 such that the internal column residue was drawn.

The hydrolytic reaction was conducted by repeating the above operations until the cumulative feed time of the liquid reaction mixture reached 800 hours. By using the formula $E = E_0 \exp(-kt)$, values of activity exhibited on and after the $100^{th}$ hour of the cumulative feed time of the liquid reaction mixture where the substantial separation of the enzyme in the initial stage no longer took place—each of said values having been calculated from its corresponding time required for the hydrolysis, its corresponding weight of the oil and the packed weight of the immobilized enzyme—were fitted. As a result, the initially exhibited activity and deactivation rate constant were found to be 1,300 U/g and $6.7 \times 10^{-4}$ 1/h, respectively.

EXAMPLE 2

An immobilized enzyme was prepared in a similar manner as in Example 1 except that "Duolite A-568" was ground and classified, a phosphate solution was used as a buffer in place of the acetate solution, the amount of the enzyme to be dissolved in the buffer upon conducting immobilization was changed to 0.39 part by weight, and rapeseed oil was used in the oil treatment applied subsequent to the post-immobilization washing. The thus-obtained immobilized enzyme had 2,643 U/g (dry weight) of hydrolytic activity (exhibitable activity), and the weight-basis average particle size of the immobilized enzyme was 311 μm (the same immobilized enzyme was used in the subsequent Examples and Comparative Example). Incidentally, the immobilized enzyme had a particle size distribution as shown in Table 2. Further, a hydrolytic reaction was conducted in a similar manner as in Example 1 except that the packed thickness of the immobilized enzyme was changed to 144 mm, the packed amount of the immobilized enzyme was changed to 16.3 g, and the rapeseed oil was used as an oil or fat raw material. In the hydrolytic reaction, the void volume of the packed layer of the enzyme was 0.518, the maximum pressure loss occurred through the packed layer was 0.35 MPa, the average droplet size of the water in the w/o liquid reaction mixture was 154 μm, and the shear stress factor applied to the surface of the immobilized enzyme was $8.14 \times 10^{-4}$ MPa. Further, the initially exhibited activity and deactivation rate constant determined in accordance with the deactivation rate formula were 2,200 U/g and $6.7 \times 10^{-4}$ 1/h, respectively.

TABLE 2

| Undersize [μm] | Oversize [μm] | Weight fraction, % |
| --- | --- | --- |
| 425 | 500 | 8.05 |
| 355 | 425 | 31.14 |
| 250 | 355 | 47.96 |
| 150 | 250 | 12.15 |
| 106 | 150 | 0.71 |
| 0 | 106 | 0 |

EXAMPLE 3

A hydrolytic reaction was conducted in a similar manner as in Example 2 except that the packed amount of the immobilized enzyme was changed to 16.5 g and the cumulative feed time of the liquid reaction mixture was changed to 400 hours. In the hydrolytic reaction, the void volume of the packed layer of the enzyme was 0.514, the maximum pressure loss occurred through the packed layer was 0.46 MPa, the average droplet size of the water in the w/o liquid reaction mixture was 93 μm, and the shear stress factor applied to the surface of the immobilized enzyme was $1.05 \times 10^{-3}$ MPa. Further, the initially exhibited activity and deactivation rate constant determined in accordance with the deactivation rate formula were 1,997 U/g and $1.58 \times 10^{-3}$ 1/h, respectively.

EXAMPLE 4

A hydrolytic reaction was conducted in a similar manner as in Example 2 except that the packed amount of the immobilized enzyme was changed to 16.8 g, the feed rate to the packed layer was changed to 40 mL/min and the cumulative feed time of the liquid reaction mixture was changed to 374 hours. In the hydrolytic reaction, the void volume of the packed layer of the enzyme was 0.505, the maximum pressure loss occurred through the packed layer was 0.36 MPa, the average droplet size of the water in the w/o liquid reaction mixture was 105 μm, and the shear stress factor applied to the surface of the immobilized enzyme was $7.94 \times 10^{-4}$ MPa. Further, the initially exhibited activity and deactivation rate constant determined in accordance with the deactivation rate formula were 1,772 U/g and $6.50 \times 10^{-4}$ 1/h, respectively.

EXAMPLE 5

A hydrolytic reaction was conducted in a similar manner as in Example 2 except that the packed amount of the immobilized enzyme was changed to 17.2 g, the feed rate to the packed layer was changed to 20 mL/min and the cumulative feed time of the liquid reaction mixture was changed to 374 hours. In the hydrolytic reaction, the void volume of the packed layer of the enzyme was 0.494, the maximum pressure loss occurred through the packed layer was 0.22 MPa, the average droplet size of the water in the w/o liquid reaction mixture was 120 μm, and the shear stress factor applied to the surface of the immobilized enzyme was $4.63 \times 10^{-4}$ MPa. Further, the initially exhibited activity and deactivation rate con-

EXAMPLE 6

A hydrolytic reaction was conducted in a similar manner as in Example 2 except that the packed amount of the immobilized enzyme was changed to 8.7 g, the packed thickness was changed to 80 mm, the feed rate to the packed layer was changed to 110 mL/min and the cumulative feed time of the liquid reaction mixture was changed to 350 hours. In the hydrolytic reaction, the void volume of the packed layer of the enzyme was 0.540, the maximum pressure loss occurred through the packed layer was 0.26 MPa, the average droplet size of the water in the w/o liquid reaction mixture was 134 µm, and the shear stress factor applied to the surface of the immobilized enzyme was $1.19 \times 10^{-3}$ MPa. Further, the initially exhibited activity and deactivation rate constant determined in accordance with the deactivation rate formula were 2,265 U/g and $1.37 \times 10^{-3}$ 1/h, respectively.

EXAMPLE 7

A hydrolytic reaction was conducted in a similar manner as in Example 2 except that the packed amount of the immobilized enzyme was changed to 14.2 g, the packed thickness was changed to 145 mm, the feed rate to the packed layer was changed to 62 mL/min and the cumulative feed time of the liquid reaction mixture was changed to 358 hours. In the hydrolytic reaction, the void volume of the packed layer of the enzyme was 0.584, the maximum pressure loss occurred through the packed layer was 0.26 MPa, the average droplet size of the water in the w/o liquid reaction mixture was 120 µm, and the shear stress factor applied to the surface of the immobilized enzyme was $7.82 \times 10^{-4}$ MPa. Further, the initially exhibited activity and deactivation rate constant determined in accordance with the deactivation rate formula were 1,765 U/g and $1.03 \times 10^{-3}$ 1/h, respectively.

EXAMPLE 8

A hydrolytic reaction was conducted in a similar manner as in Example 2 except that the packed amount of the immobilized enzyme was changed to 13.9 g, the feed rate to the packed layer was changed to 40 mL/min and the cumulative feed time of the liquid reaction mixture was changed to 474 hours. In the hydrolytic reaction, the void volume of the packed layer of the enzyme was 0.591, the maximum pressure loss occurred through the packed layer was 0.21 MPa, the average droplet size of the water in the w/o liquid reaction mixture was 120 µm, and the shear stress factor applied to the surface of the immobilized enzyme was $6.56 \times 10^{-4}$ MPa. Further, the initially exhibited activity and deactivation rate constant determined in accordance with the deactivation rate formula were 1,408 U/g and $2.80 \times 10^{-4}$ 1/h, respectively.

EXAMPLE 9

A hydrolytic reaction was conducted in a similar manner as in Example 2 except that the packed amount of the immobilized enzyme was changed to 14.3 g, the feed rate to the packed layer was changed to 20 mL/min and the cumulative feed time of the liquid reaction mixture was changed to 474 hours. In the hydrolytic reaction, the void volume of the packed layer of the enzyme was 0.579, the maximum pressure loss occurred through the packed layer was 0.08 MPa, the average droplet size of the water in the w/o liquid reaction mixture was 120 µm, and the shear stress factor applied to the surface of the immobilized enzyme was $2.38 \times 10^{-4}$ MPa. Further, the initially exhibited activity and deactivation rate constant determined in accordance with the deactivation rate formula were 1,229 U/g and $2.50 \times 10^{-4}$ 1/h, respectively.

EXAMPLE 10

A hydrolytic reaction was conducted in a similar manner as in Example 2 except that the packed amount of the immobilized enzyme was changed to 15.7 g, the packed thickness was changed to 135 mm, the cumulative feed time of the liquid reaction mixture was changed to 361 hours, and the liquid reaction mixture was fed by a circulating pump 17 to an emulsifier 16 ("MILDER MDN303", trade name; manufactured by Ebara Corporation) through a substrate circulation bypass line 15 and was returned in an emulsified form to the substrate circulating tank 2. In the hydrolytic reaction, the void volume of the packed layer of the enzyme was 0.506, the maximum pressure loss occurred through the packed layer was 0.6 MPa, the average droplet size of the water in the w/o liquid reaction mixture was 43 µm, and the shear stress factor applied to the surface of the immobilized enzyme was $1.42 \times 10^{-3}$ MPa. Further, the initially exhibited activity and deactivation rate constant determined in accordance with the deactivation rate formula were 1,835 U/g and $2.02 \times 10^{-3}$ 1/h, respectively.

EXAMPLE 11

Figure 4:
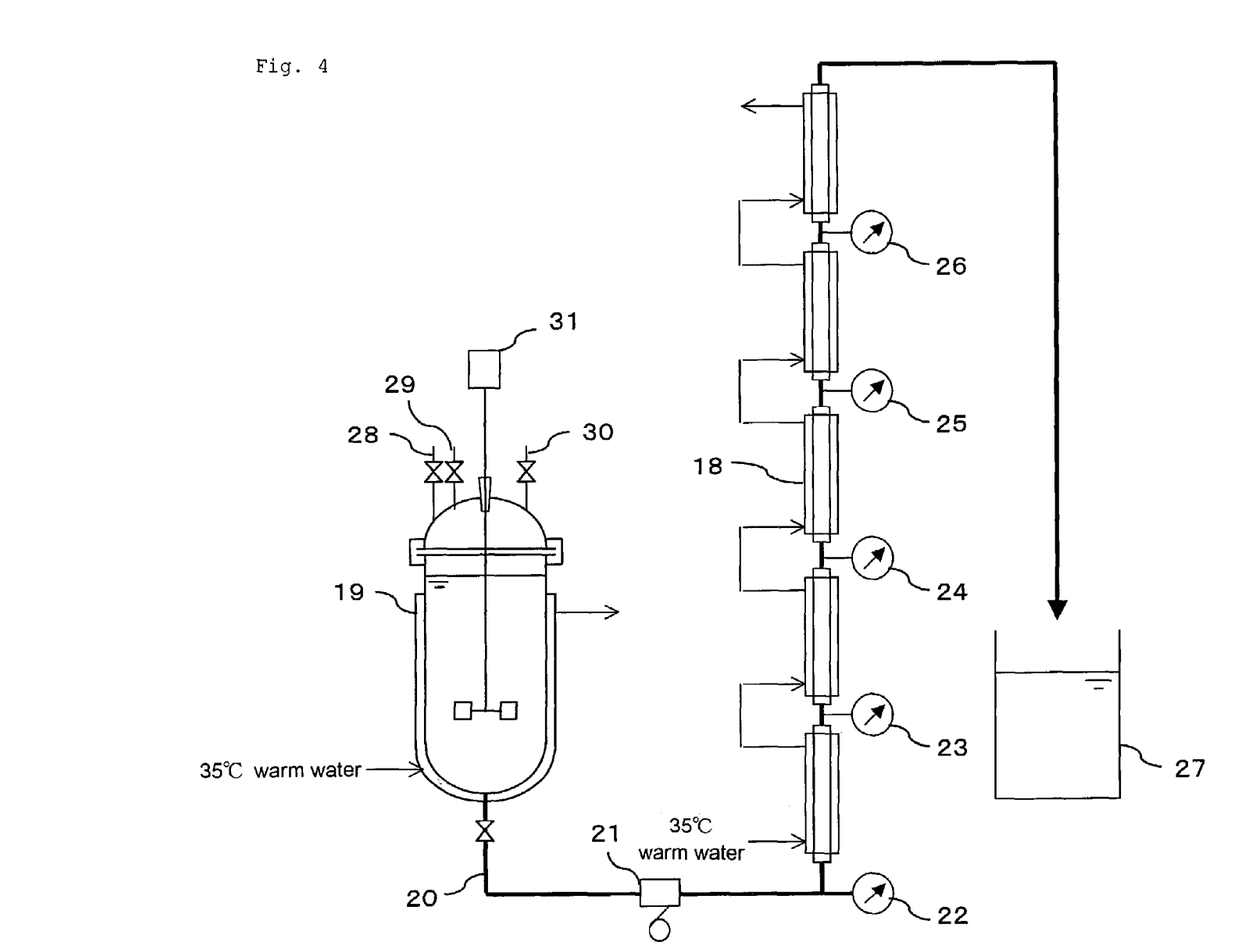
FIG. 4 is a flow diagram of a continuous hydrolysis reactor.

Equipment used for the continuous hydrolytic reaction is illustrated in FIG. 4.

An enzyme column 18 of 10 mm in inner diameter and 1,000 mm in height (5 columns of 200 mm each) was packed with 27.3 g (dry weight basis) of the immobilized enzyme. The void volume $\epsilon$ of the packed layer was calculated to be 0.429 based on the packed bulk specific gravity $\rho_1$ of 0.348 g/cm$^3$. The refined rapeseed oil and deionized water were charged into a substrate-supplying tank 19, which was 100 mm in inner diameter and 2.5 L in capacity and was equipped with an agitating blade of 50 mm in diameter, such that the weight ratio of the substrates (deionized water [g]/refined rapeseed oil [g]) became 0.6. The substrate was then heated to 35 C.° in 10 minutes while mixing them at 400 r/min. The average droplet size of the water in the w/o liquid reaction mixture was 120 µm. The reaction mixture was continuously supplied to the column 18 packed with an immobilized enzyme through the substrate feed line 20 at flow rate of 1.6 mL/min by feed pump 21. The substrate-supplying tank 19 was occasionally supplied with the substrate (weight ratio of water to oil, 0.6) so as to maintain the total substrate content to a maximum of 2000 g or less. During the reaction, the pressure was monitored by the pressure gauges 22 through 26 and the liquid reaction mixture was periodically sampled through the reaction mixture-exhausting line 27 to determine the degree of hydrolysis of the oil. The degree of hydrolysis of the oil was calculated in accordance with (acid value/saponification value)×100 (%). The pressure loss of the packed layer with an immobilized enzyme per unit thickness of the packed layer was calculated based on the slope obtained from an approximation formula established on the basis of pressure values recorded by the pressure gauges 22 through 26. The approximation formula can be established by approximating the values by an appropriate function such as a polynomial equation. The pressure value and the pressure loss are as shown in Table 3.

The pressure loss was at the highest near the inlet of the packed layer, and the shear stress factor expressed by the formula (1) applied to the surface of the immobilized enzyme was 2.3×10$^{-4}$ MPa. The continuous reaction was conducted until the cumulative feed time of the liquid reaction mixture reached 343 hours. By using the formula E=E$_0$ exp (−kt), values of activity exhibited on and after the 100$^{th}$ hour of the cumulative feed time of the liquid reaction mixture where the substantial separation of the enzyme in the initial stage no longer took place—each of said values having been calculated from weight of the oil existing inside the column and the packed weight of the immobilized enzyme; and a detention period of the reaction mixture within the column and a decomposition rate—were fitted. As a result, the initially exhibited activity and deactivation rate constant were found to be 768 U/g and 5.3×10$^{-5}$ 1/h, respectively.

TABLE 3

| The packed thickness from inlet (mm) | Pressure (MPa) | Pressure loss per packed thickness (MPa/m) |
| --- | --- | --- |
| 0 | 0.48 | 0.687 |
| 200 | 0.35 | 0.562 |
| 400 | 0.26 | 0.491 |
| 600 | 0.15 | 0.426 |
| 800 | 0.07 | 0.355 |

COMPARATIVE EXAMPLE 1

A hydrolytic reaction was conducted in a similar manner as in Example 2 except that the packed amount of the immobilized enzyme was changed to 15.7 g, the packed thickness was changed to 135 mm, the cumulative feed time of the liquid reaction mixture was changed to 361 hours, and the liquid reaction mixture was fed by the circulating pump 17 to two emulsifiers 16 ("MILDER MDN303", trade name; manufactured by Ebara Corporation) through the substrate circulation bypass line 15 and was returned in an emulsified form to the substrate circulating tank 2. In the hydrolytic reaction, the void volume of the packed layer of the enzyme was 0.506, the maximum pressure loss occurred through the packed layer was 0.72 MPa, the average droplet size of the water in the w/o liquid reaction mixture was 35 µm, and the shear stress factor applied to the surface of the immobilized enzyme was 1.7×10$^{-3}$ MPa. Further, the initially exhibited activity and deactivation rate constant determined in accordance with the deactivation rate formula were 2,100 U/g and 2.9×10$^{-3}$ 1/h, respectively.

Figure 2:
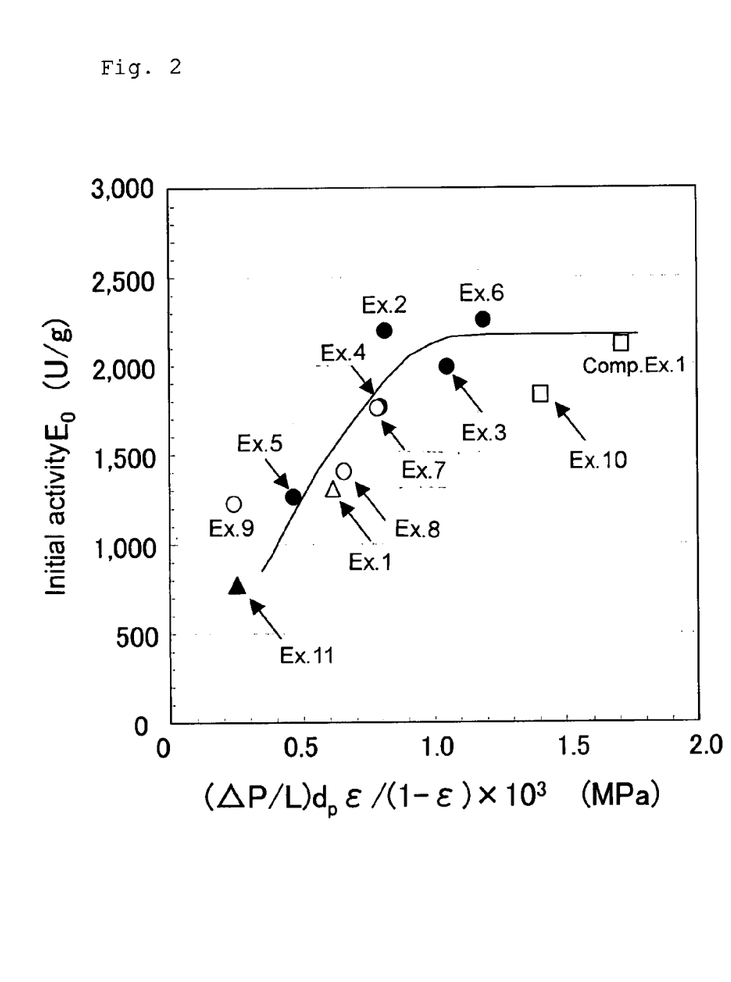
FIG. 2 diagrammatically shows initially exhibited activities as a function of shear stress factor.
Figure 3:
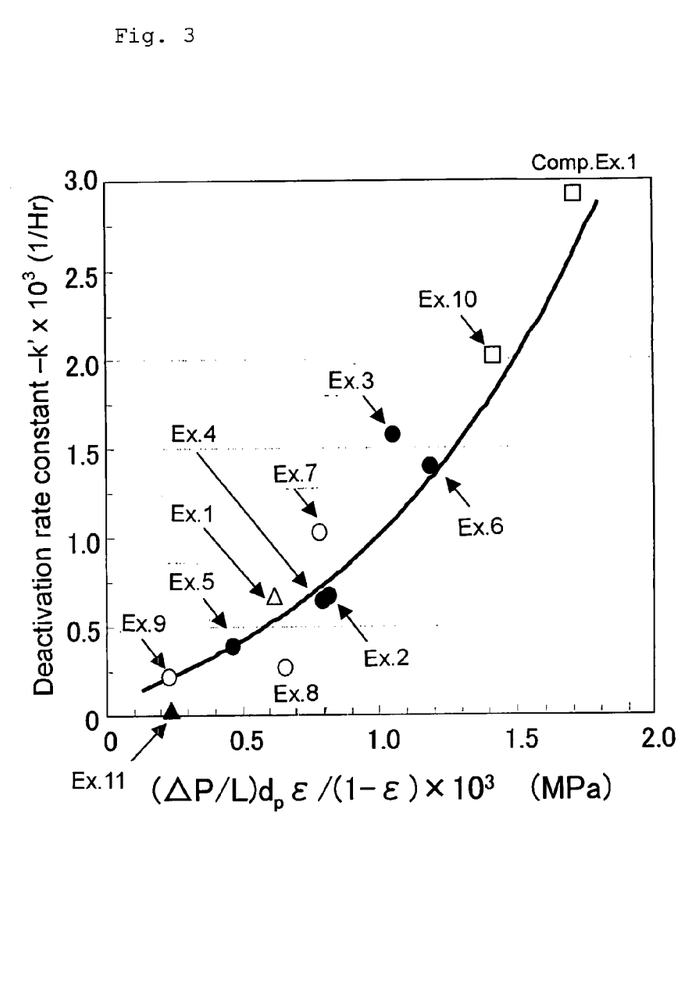
FIG. 3 diagrammatically illustrates deactivation rate constants as a function of shear stress factor.

The results of the measurements in the Invention Examples and Comparative Example are shown in FIGS. 2 and 3. A large shear stress factor results in high initially developed activity and hence, can make the equipment compact. However, the large shear stress also leads to an increase in deactivation rate factor, a decrease in the serviceability of immobilized enzyme, and an increase in the frequency of replacement of the immobilized enzyme.

The invention claimed is:

1. A process for hydrolyzing an oil or fat by mixing an oil-phase substrate and a water-phase substrate and feeding them as a water-in-oil emulsion to a packed layer with an immobilized enzyme immobilized on particles packed therein, wherein said oil or fat is subjected to a hydrolytic reaction under feeding conditions such that a shear stress factor (τw), is within a range of from 1 ×10$^{-4}$ to 1.4–10$^{-3}$ MPa, which is applied to a surface of said immobilized enzyme and is expressed by the following formula (1):

$$\tau w = (\Delta P/L) \times dp \times \epsilon/(1-\epsilon) \qquad (b\,1)$$

wherein ΔP represents a maximum pressure loss [MPa] through said packed layer during said hydrolytic reaction, L represents a thickness [m] of said packed layer, dp represents a weight-basis average particle size [m] of particles of said packed, immobilized enzyme, and ϵ represents a void volume [−] of said packed layer.

2. A process according to claim 1, wherein said water-in-oil emulsion has an average droplet size of from 40 to 200 µm.

3. A process according to claim 1, wherein said shear stress factor (τw) is 1 ×10$^{-4}$ to 1×10$^{-3}$ MPa.

4. A process according to claim 1, wherein said oil or fat is a triglyceride.

5. A process according to claim 1, wherein said immobilized enzyme is lipase.

6. A process according to claim 1, wherein said immobilized enzyme is lipase immobilized on an anion exchange resin.

7. The process of claim 1, wherein 25 to 100 parts by weight of said water-phase substrate are mixed with 100 parts by weight of said oil-phase substrate.

8. The process of claim 1, wherein said immobilized enzyme is an esterase.

9. The process of claim 1, wherein said immobilized enzyme is comprised of 0.05 to 10 parts by weight of said enzyme per part by weight of said immobilization carrier.

10. The process of claim 1, wherein a linear feeding rate of said water-in-oil emulsion is 10 to 300 mm/min.

* * * * *

UNITED STATES PATENT AND TRADEMARK OFFICE
CERTIFICATE OF CORRECTION

PATENT NO. : 7,517,674 B2 Page 1 of 1
APPLICATION NO. : 11/144780
DATED : April 14, 2009
INVENTOR(S) : Toshiteru Komatsu et al.

It is certified that error appears in the above-identified patent and that said Letters Patent is hereby corrected as shown below:

Column 14, line 16, Claim 1, "is within a range from $1 \times 10^{-4}$ to $1.4\text{-}10^{-3}$" should read -- is within a range from $1 \times 10^{-4}$ to $1.4 \times 10^{-3}$ --.

Signed and Sealed this

Twenty-third Day of June, 2009

JOHN DOLL
*Acting Director of the United States Patent and Trademark Office*